(12) United States Patent
Vernest et al.

(10) Patent No.: US 9,952,744 B2
(45) Date of Patent: Apr. 24, 2018

(54) CROWDSOURCED DETERMINATION OF MOVABLE DEVICE LOCATION

(71) Applicants: Kyle Vernest, Boston, MA (US); David M. T. Ting, Sudbury, MA (US); Alain Slak, Bedford, MA (US); Evan Hoyt, Lexington, MA (US)

(72) Inventors: Kyle Vernest, Boston, MA (US); David M. T. Ting, Sudbury, MA (US); Alain Slak, Bedford, MA (US); Evan Hoyt, Lexington, MA (US)

(73) Assignee: IMPRIVATA, INC., Lexington, MA (US)

( * ) Notice: Subject to any disclaimer, the term of this patent is extended or adjusted under 35 U.S.C. 154(b) by 333 days.

(21) Appl. No.: 14/945,646

(22) Filed: Nov. 19, 2015

(65) Prior Publication Data

US 2016/0139744 A1    May 19, 2016

Related U.S. Application Data

(60) Provisional application No. 62/081,820, filed on Nov. 19, 2014, provisional application No. 62/183,793, filed on Jun. 24, 2015.

(51) Int. Cl.
| | |
|---|---|
| *G06F 3/0482* | (2013.01) |
| *G06F 3/0484* | (2013.01) |
| *H04L 29/08* | (2006.01) |
| *H04L 12/24* | (2006.01) |
| *G06F 19/00* | (2018.01) |
| *H04W 4/04* | (2009.01) |
| *G06Q 50/22* | (2018.01) |
| *H04L 29/06* | (2006.01) |
| *H04W 4/02* | (2018.01) |
| *H04W 64/00* | (2009.01) |
| *H04W 60/04* | (2009.01) |
| *H04W 12/06* | (2009.01) |

(52) U.S. Cl.
CPC ........ *G06F 3/0482* (2013.01); *G06F 3/04842* (2013.01); *G06F 19/327* (2013.01); *G06Q 50/22* (2013.01); *H04L 41/22* (2013.01); *H04L 63/08* (2013.01); *H04L 67/12* (2013.01); *H04L 67/18* (2013.01); *H04L 67/22* (2013.01); *H04W 4/023* (2013.01); *H04W 4/043* (2013.01); *H04W 64/00* (2013.01); *H04W 12/06* (2013.01); *H04W 60/04* (2013.01)

(58) Field of Classification Search
None
See application file for complete search history.

(56) References Cited

U.S. PATENT DOCUMENTS

| | | | | |
|---|---|---|---|---|
| 2011/0103360 A1* | 5/2011 | Ku | ............ | G01S 5/021 370/338 |
| 2013/0197974 A1* | 8/2013 | Romanko | ............ | G06Q 30/06 705/7.33 |
| 2013/0332553 A1* | 12/2013 | Hung | ............ | H04L 12/1886 709/206 |

* cited by examiner

*Primary Examiner* — Tuan S Nguyen
(74) *Attorney, Agent, or Firm* — Morgan, Lewis & Bockius LLP

(57) ABSTRACT

The locations of electronic devices in an institutional facility are determined based on crowdsourced location reporting by users in an institutional setting and responding to device location queries.

20 Claims, 3 Drawing Sheets

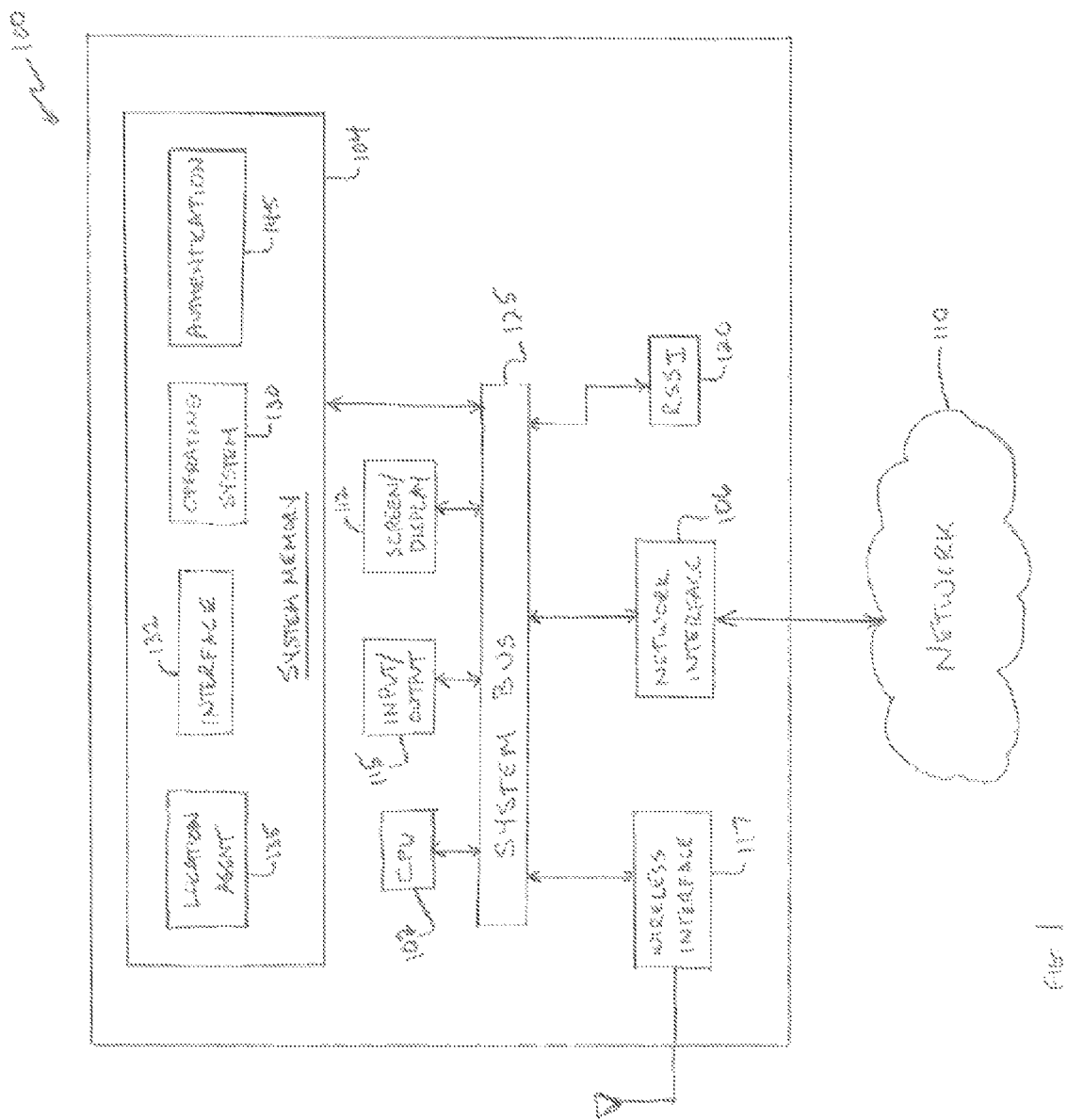

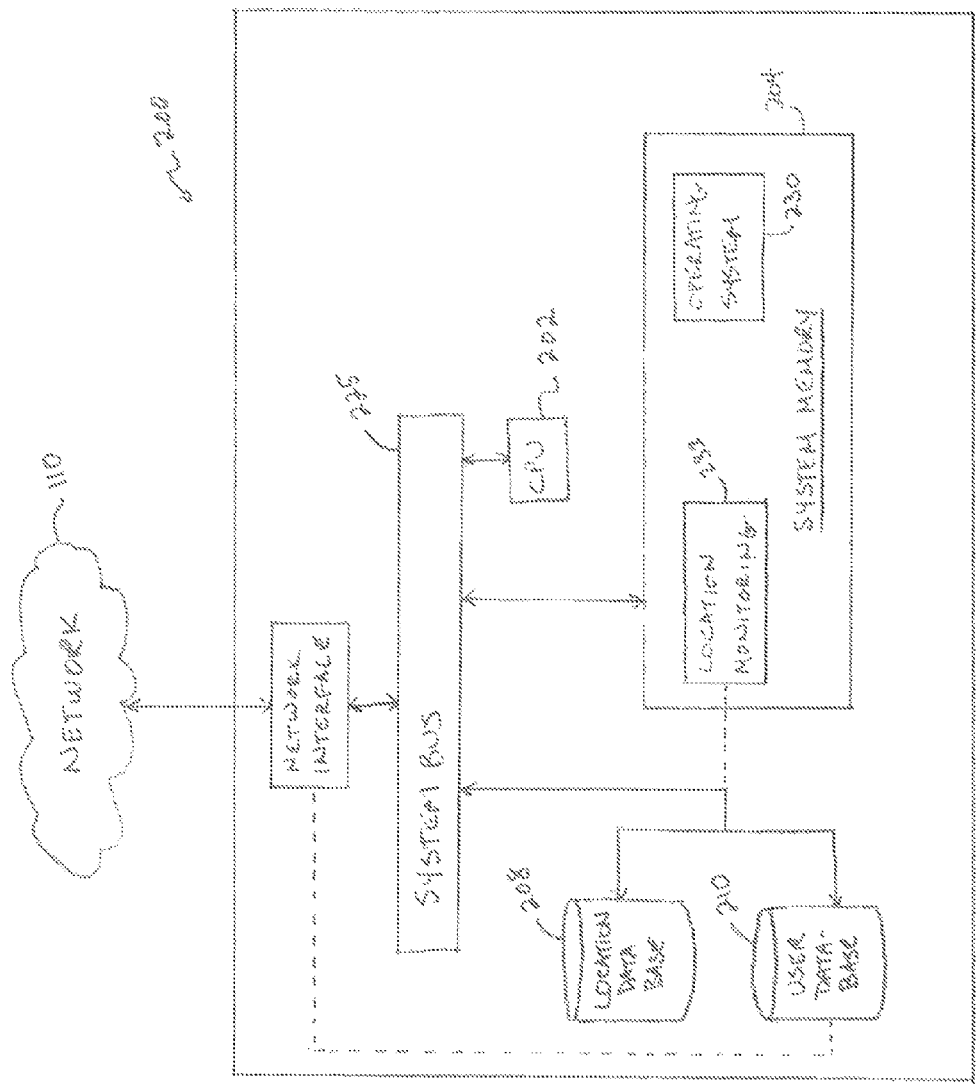

| Device | Last Update | Building | Wing | Department | Room | Associated Devices |
|---|---|---|---|---|---|---|
| Workstation Tower.surg.54 | 10/31/2015 13:05:01 | 75 Francis | Tower | Surgery | 10-313 | |

CROWDSOURCED DETERMINATION OF MOVABLE DEVICE LOCATION

RELATED APPLICATION

This application claims the benefit of and priority to U.S. Provisional Patent Application Nos. 62/081,820, filed Nov. 19, 2014, and 62/183,793, filed Jun. 24, 2015, the entire disclosures of which are hereby incorporated by reference.

TECHNICAL FIELD

The invention relates generally to healthcare information technology, and in particular to systems and methods for location-based management of data, access control, and clinical collaboration.

BACKGROUND

In a busy healthcare environment, such as a hospital, clinicians roam frequently among patients, floors and buildings. Each time a clinician reaches a new location, she may require access to patient information or other medical data maintained by the facility (or elsewhere). That data may be accessed via a local, typically shared workstation, or via a handheld wireless device, such as a "smart phone" or tablet capable of hosting applications and establishing telecommunications, Internet and/or local intranet connections.

In particular, medical institutions from hospitals to physician practice groups to testing centers maintain diverse electronic medical records (EMR) systems, which collectively form the healthcare information backbone. EMR systems allow clinicians access to medical information maintained in various back-end systems. The typical workflow when a physician interacts with a patient involves first logging onto the computer system, then launching and logging into one or more EMR applications, selecting the right patient record, verifying that the record matches the patient, reviewing results (often from different sources), checking up on medical references, entering orders or prescriptions (e.g., using computerized physician order entry (CPOE) applications and ePrescribing), and/or charting patient progress. All of these activities may involve the same patient but different applications, and in some cases multiple separate applications for a single patient-specific activity.

Moreover, healthcare records are protected by strict privacy laws (such as the Health Insurance Portability and Accountability Act, or HIPAA), regulatory regimes, and institutional access policies. Accordingly, when a clinician moves from place to place, he may be required to log on to a new terminal or device, and because of data-access restrictions, the log-on procedure may involve cumbersome and/or multiple authentication modalities. Depending on system configuration, the clinician may be required to re-launch the applications that were running on the previously used device. Therefore, there is a need for systems that streamline or avoid authentication procedures and provision a workspace for clinicians on the move, and this, in turn, may depend on knowledge of a clinician's physical location within a facility. Knowledge of a particular individual's location may be obtained in various ways, including from the location of a device with which she interacts—assuming, of course that the device location is accurately known. In a large facility, even seemingly "fixed" devices such as workstations can be moved periodically, and mobile workstations obviously change location frequently.

For example, the location of a device may be specified by global-positioning system (GPS) coordinates, and if the node is equipped with a GPS chipset, its location can be updated as it is moved. Unfortunately, many workstations and other devices are not GPS-equipped, and indeed, GPS tracking is not always possible even for devices that are GPS-enabled; for example, GPS often does not work well within buildings.

SUMMARY

Embodiments of the present invention focus on determining the location of computational or other devices with which clinicians interact. These devices, which include workstations, thick or thin client devices, kiosks, and network-connected medical devices are herein referred to collectively as "nodes." In general, a node is able to access, via a network, one or more data stores that include information (e.g., EMR) of interest to clinicians. The term "network" is herein used broadly to connote wired or wireless networks of computers or telecommunications devices (such as wired or wireless telephones, tablets, etc.). For example, a computer network may be a local area network (LAN) or a wide area network (WAN). When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), Bluetooth, Zigbee, IrDa, near-field communication (NFC), or other suitable protocol. Furthermore, components of the system may communicate through a combination of wired or wireless paths, and communication may involve both computer and telecommunications networks. For example, a user may establish communication with a server using a "smart phone" via a cellular carrier's network (e.g., authenticating herself to the server by voice recognition over a voice channel); alternatively, she may use the same smart phone to authenticate to the same server via the Internet, using TCP/IP over the carrier's switch network or via Wi-Fi and a computer network connected to the Internet.

Crowdsourcing of location involves prompting users to specify the location of the nodes with which they interact. For example, during a user log-on procedure, the user may be prompted to enter the location of the node along with her usual credentials. To avoid overburdening users, only one user within a defined period of time (e.g., a day) may be prompted to enter this information if a node is unlikely to be moved frequently. As used herein, the term "location" broadly connotes precise or approximate spatial coordinates or a map point, presence within a defined physical area, or proximity to a known place, entity, person, or device. For example, a location may correspond to a room number or absolute global positioning system (GPS) coordinates, a more general category—department, floor, etc.—or proximity to a device such as reader, a mobile telecommunication device, a beacon, a piece of medical equipment, etc.

Accordingly, in a first aspect, the invention relates to a method of establishing a location of a device in an institutional space. In various embodiments, the method comprises the steps of providing a device-location database storing records for each of a plurality of devices registered in the database as located in the institutional space. The database electronically store, for each device, a record specifying a location of the device within the institutional space and when the location was most recently updated. At the device, a request of a user for log-on and authentication is registered, and in response to the request, the user is prompted for authentication information and, depending on how recently the database record corresponding to the device was updated, the current location of the device. If the current location was obtained from the user, the current location and the time it was obtained may be stored in the database record corresponding the device.

In some embodiments, prompting the user for the current location of the device comprises providing a selection menu of location types, the location types including at least a location area and/or proximity to a fixture. For the location area, the selection menu may comprise identifiers of a building, a wing, a room, a floor, and/or a department; for the fixture, the selection menu may comprise identifiers of a telecommunication device, a piece of medical equipment, and/or a personnel station.

In some embodiments, the user is prompted for a location if an interval between the current time and the time when the database record corresponding to the device was last updated exceeds a threshold. When the threshold is exceeded, a plurality of users may be prompted for a current location of the device, and the current locations provided by the plurality of users may be correlated to determine consistency thereamong prior to causing the current location to be stored in the database. The threshold may depend on the frequency with which the location of the device changes.

In some embodiments, the method further comprises computationally maintaining, for each of a plurality of users, a score corresponding to a frequency at which the user responds to prompts for a current location, the user prompted for a current location being selected from among the plurality of users based on the user's score. A score may also reflect precision levels of the associated user's responses.

In various embodiments, the method may further comprise obtaining from the location database a location of at least one other device associated with the device, and determining whether the other device is proximate to the device. The other device may be a fixed device and the user-provided current location may be stored in the database only if the device is determined to be proximate to the fixed device. Determining whether the other device is proximate to the device may comprise wirelessly detecting, by the device and by the other device, a user's wireless device; determining an elapsed time between the wireless detections; and comparing the elapsed time to a threshold.

In another aspect, the invention pertains to a system for establishing and storing locations of devices in an institutional space. In various embodiments, the system comprises a plurality of devices and a location server in operative communication with the devices. The location server includes computer storage defining a device-location database, and the database includes, for each device, a record specifying a location of the device within the institutional space and when the location was most recently updated. Each of the devices includes an authentication module and is configured to (i) register a request of a user for log-on and authentication, (ii) in response to the request, prompt the user for authentication information, and (iii) depending on how recently the database record corresponding to the device was updated, prompt the user for a current location of the device. The location server is configured to (i) receive, from the devices, current locations provided by users of the devices and times when the current locations were obtained, and (ii) store the current locations in the database records corresponding to the devices.

In various embodiments, each of the devices includes a display and an interface for operating the display. The interface is configured to prompt the user for the current location by providing on the display a selection menu of location types, and the location types include at least a location area and/or proximity to a fixture. For the location area, the selection menu may comprise identifiers of a building, a wing, a room, a floor, and/or a department. For the fixture, the selection menu may comprise identifiers of a telecommunication device, a piece of medical equipment, and/or a personnel station.

The location server may be configured to notify a device if an interval between the current time and the time when the device-location database record corresponding to the device was last updated exceeds a threshold. The device may be configured, upon receipt of the notification, to cause the interface to prompt a user for a location. In some embodiments, the device is further configured, when the threshold is exceeded, to cause the interface to prompt a plurality of users for a current location of the device and to transmit the plurality of current locations to the location server; and the location server is further configured to correlate the plurality of current locations to determine consistency thereamong prior to storing the current location in the device-location database.

The computer storage may further define a user database including, for each of a plurality of users, a score corresponding to a frequency at which the user responds to prompts for a current location. The location server is then further configured to transmit, to the devices, identifiers of users who should be prompted for a current location based on the user scores. The user's score may also reflect precision levels of the user's responses. The threshold may depend on the frequency with which the location of the device changes.

In various embodiments, the records of the device-location database also include, for at least some of the devices, an identifier of at least one other device associated therewith. If a device associated with a current device is a fixed device, the current location received from the current device is stored in the device-location database only if the device is determined to be proximate to the fixed device.

The location server may be configured to receive notifications, from the device and the fixed device, of wireless detection of a user's wireless device, determine an elapsed time between the wireless detections, and determine whether the other device is proximate to the device by comparing the elapsed time to a threshold.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, routines, steps, or characteristics may be combined in any suitable manner in one or more examples of the technology. As used herein, the terms "approximately" and "substantially" mean ±10%, and in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1 schematically illustrates a node in accordance with embodiments of the invention.

FIG. 2 schematically illustrates a server in accordance with embodiments of the invention.

DETAILED DESCRIPTION

Figures 3A, 3B:
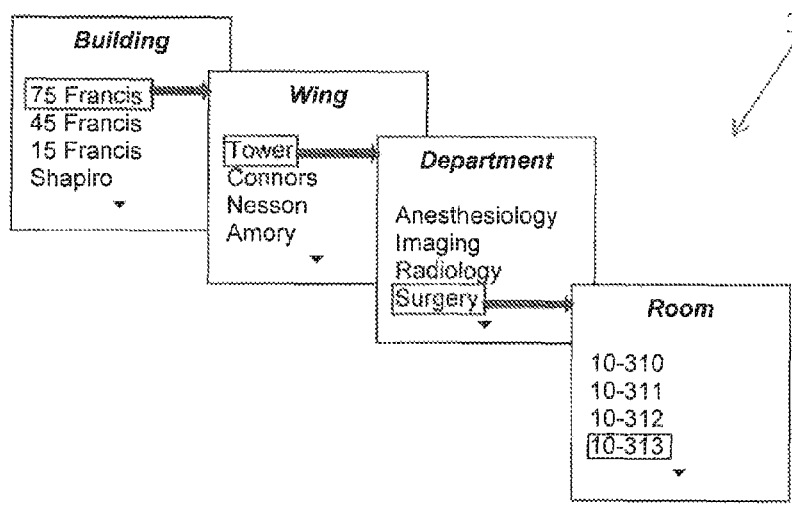
FIGS. 3A and 3B show, respectively, a database entry and the operation of an interface facilitating entry of the data.

Refer first to FIG. 1, which illustrates a representative node 100. The node 100 may be a workstation (e.g., a general-purpose personal computer running suitable software), a thick or thin client device, a kiosk, a network-connected medical device, or any other device with which clinicians and other users interact, and which may be moved from time to time within an institutional setting. Node 100 typically includes a processor 102 (e.g., a CPU microprocessor) and associated system memory 104, a network interface 106 (for connection to the institutional network 110 and/or the Internet), and, usually, one or more non-volatile digital storage elements (such as a hard disk, CD, DVD, USB memory key, etc.) and associated drives. Further, workstation 100 includes user input/output devices such as a display screen 112 and conventional tactile input devices 115 such as keyboard and mouse or touch pad. A wireless interface 117, which may be separate from or implemented within network interface 106, facilitates wireless communication with user mobile devices. In some embodiments, workstation 100 includes a received signal-strength indication (RSSI) circuit 120, which, again, may be implemented within or separate from network interface 106. The various components communicate with each other via one or more buses 125.

In use, processor 102 executes one or more computer programs (conceptually illustrated as program modules) stored in system memory 104. An operating system 130 (such as, e.g., MICROSOFT WINDOWS, UNIX, LINUX, iOS, or ANDROID) provides low-level system functions, such as file management, resource allocation, and routing of messages from and to hardware devices (such as I/O device (s) 115) and one or more higher-level user applications (such as EMR applications, office programs, a web browser, etc.) An interface 132 generates screen displays and receives user input via the input devices, e.g., by the user's typing on the keyboard, moving the mouse, or clicking with the mouse on a displayed control element.

A location agent 135 determines whether to solicit location information for the workstation 100 from a user who has just logged in. To obtain that information, location agent 135 generates (or causes interface 132 to generate) control elements for presentation on display 112, and which the user can operate to provide the requested location information.

In some implementations, node 100 includes an authentication agent 145 that allows a user to obtain access to restricted data consistent with his privilege level and the security policies of the institution. Authentication agents are known in the art and described, for example, in U.S. Ser. No. 11/294,354, filed Dec. 5, 2005, the entire disclosure of which is hereby incorporated by reference.

FIG. 2 illustrates a location server that also typically includes a processor 202 (e.g., a CPU) and associated system memory 204, a network interface 206, a system bus 225, and one or more non-volatile digital storage elements including a location database 208 and a user database 210. The databases 208, 210 may be stored locally as separate files or disk partitions, or may be stored remotely and accessed via network interface 206. Location database 208 stores records each specifying a node and its most recently determined location, as well as, typically, its distance from other nodes.

System memory 204 includes stored instructions defining an operating system 230 and high-level applications (not shown). In addition, memory 204 stores a location-monitoring application 233 that determines which users to solicit for location information and when. More generally, server 200 may be implemented on any suitable computing platform including a processing unit, a system memory, and a system bus that couples various system components including the system memory to the processing unit. During operation, the system memory contains the instructions implementing the functionality described herein. Computers typically include a variety of computer-readable media that can form part of the system memory and be read by the processing unit. By way of example, and not limitation, the system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data. The operating system may be or include a variety of operating systems such as Microsoft WINDOWS operating system, the Unix operating system, the LINUX operating system, the Xenix operating system, the IBM AIX operating system, the Hewlett Packard UX operating system, the MACINTOSH operating system, the APACHE operating system, an OPENSTEP operating system or another operating system of platform.

In a representative operational sequence, the node 100 registers the request of a user to log-on, which may involve authentication via authentication module 145. Interface 132 generates a prompt for authentication information, which may be passed via network 110 to an authentication server. Location agent 135 notifies location-monitoring module 233 of location server 200 of the log-on request and the identity of the user. Depending on factors discussed below, including, e.g., how recently the device's location was updated and when the user was last issued a location query, the user may be asked to provide the location of device 100.

The user's response is used to update the record of device 100 in location database 208, which stores the latest location information for each node in the network whose location is monitored. The degree of location specificity at a given time may depend on the level of information provided by users in response to location queries. This is illustrated in the exemplary location record 300 in FIG. 3A. The record includes fields identifying a device, when the record was last updated, any devices associated for location purposes with the identified device, and a series of progressively more granular identifiers of the device location: Building, Wing, Department, and Room. The number of location fields that actually contain data for a particular device depends on the amount of information provided by queried users. In the illustrated record 300, a workstation identified as Tower.surg.54 had its location last updated on Oct. 31, 2015. The boldfaced entry "Surgery" indicates that the Department field received the most recent update, i.e., Room 10-313 no longer reflects the most current information.

User database 210 contains records for each user in the network specifying a score and the last time the user was asked for location information. The user's score reflects a degree of responsiveness to location requests. For example, a user who responds to a location request may receive points based on the granularity of his response; while a harried user may not know he is in room 10-313 if this is not prominently numbered, he should be aware of the department or at least the building wing.

Location-monitoring module 233 may issue queries to update the location of a device at fixed intervals depending on the device, the importance of knowing its current location and how frequently it is likely to be moved. A highly utilized workstation that is rarely moved, for example, need not have its location updated many times a day as different users log on, while conversely, the administrator may designate some machines as mobile, i.e., untracked, so users are not asked to report locations for those machines. Moreover, the less urgent the need for a location update, the more discriminating location-monitoring module 233 can be in selecting a user, or multiple users simultaneously, for query. For example, if the current user at a device has a low score or was just recently queried for a location (e.g., at a different device), location-monitoring module 233 may wait for the next user to log on before issuing the query. In addition, module 233 may operate adaptively based on how often a device is moved (which may be determined, for example, based on how much information in a device record changes from one update to the next), gradually adjusting the frequency with which new location information is obtained to conform to a time-averaged interval between observed changes.

The interface 132 and location agent 135 of node 100 generate control elements that facilitate user provision of location information. A representative selection-based scheme, illustrated in FIG. 3B, includes a series of drop-down menus collectively indicated at 310. These request progressively more detailed location area information: as the user mouses over an entry in one menu, a new menu offers selections consistent with and more granular than in the previous menu. The user can stop at any point. Thus, the illustrated sequence of selections populates the record 300 in FIG. 3A.

Other interface designs are possible. For example, instead of or in addition to a location area, the menus may allow the user to designate proximity to a fixture—e.g., a telecommunication device, a piece of medical equipment, or a personnel station. Alternatively, the user may simply be prompted to enter the location to the best of his knowledge, or the nearest landmark, in a natural language. The response can be parsed by location-monitoring module 233 using conventional analysis tools in order to extract relevant location information.

Functionality may be allocated between nodes and location server 200 according to design preferences. For example, location server 200 can continuously poll nodes or receive notifications when users first log on to a node and thereby maintain a high awareness of current usage. In such implementations, location-monitoring module 233 may make query decisions based in part on who has just logged on to a node whose location should be updated (as determined by update criteria associated with that node, per the above discussion). Alternatively, when location-monitoring module 233 determines that a the location of a node should be updated, it can simply send an update request to the node via network 110. The location agent 135 associated with the node waits for the next suitable opportunity to obtain location information from a user, which it transmits to location server 200. The occurrence of the next suitable opportunity can depend on various factors, and can reflect a desired division of responsibility between node 100 and location server 200. For example, the update request from server 200 may contain an urgency level. If the urgency is high, location agent 135 may simply solicit location information from the next user who logs in. If the urgency is not high, location agent 135 may send the identity of the next user to server 200, whereupon location-monitoring module 233 obtains the user's current score from user database 210. If the current score exceeds a threshold and the most recent solicitation of the user for a location was longer ago than a minimum time period, location-monitoring module 233 may prompt the location agent 135 of the node to ask the current user for location information following the log-in procedure. Alternatively, location agent 135 may maintain user information locally and select among users based on the urgency the request and the locally stored information. In any case, when the user provides information, location-monitoring module 233 updates her score in user database 210.

Since it is conceivable that users might make mistakes in identifying locations, node 100 may solicit location information from multiple users within a defined time period. Alternatively or in addition, location-monitoring module 233 may corroborate a location by retrieving, or requesting an update of, the location of a device designated in the relevant record as an associated device. Associated devices generally share the same location (at some level of granularity), so consistency among listed locations is at least corroborative of accurate reporting. Moreover, the consistency of the information also reflects on the reliability of the users who contributed that information. Thus, it is possible to track the reliability of information provided by a user by evaluating how it compares to the group consensus. Users who provide more accurate results are prompted more frequently for information.

Corroboration can also be provided based on known proximities among nodes, e.g., based on a map-like or hierarchical representation maintained by location server 200. Thus, a user may be prompted to specify if she is near another device or location normally found close to the machine in question. This feature might be used, for example, to establish the reliability of a new user—i.e., the user is asked to provide not only the location of the machine on which he is working, but also that of a nearby machine, feature or installation (e.g., are you close to the nursing station or are you near the dispensing cabinet?).

Still another form of location corroboration is provided by wireless modalities, such as Bluetooth Low Energy. For example, Bluetooth can be used to identify nearby devices and ensure they are in proximity to related nodes, consistent with "related device" information in location database 208. Alternatively, partial knowledge of location provided by wireless links can be used to limit the drop-down menus presented to a user so that only the missing (and generally more specific) location information is solicited. This also provides another way of determining when a device has moved, as the set of "visible" wireless devices will change.

Indeed, interactions among wireless device can enable crowdsourcing to occur autonomously to some extent. Users' devices can be configured to report detected Bluetooth or near-field devices in order to determine which nodes are (relatively) close to each other. The number of times neighboring devices are detected may be assessed to resolve ambiguity in cases where another device "flickers" and gets detected because something changed in the propagation path. An advantage of obtaining data from users' devices (as opposed to obtaining data from the endpoint Bluetooth devices) is that the effects of barriers in the environment that limit the transmission of Bluetooth signals can be mitigated. For example, if there is an endpoint inside of a room and another endpoint just outside the same room, the room's wall may prevent the nodes from detecting each other. However, if a user with a Bluetooth device is standing in or near the room's doorway, the device may be able to detect both endpoints, thereby determining that they are in close proximity. Detected devices in proximity to a known device can also be used to update the location of the known device if the former, but not the latter, can be tracked directly. When one or more of the tracked devices moves, for example, but remains within Bluetooth (or other short-range protocol) distance of the known device, the location of the latter can be updated to that of the tracked device(s).

Once a device's location is defined, it can be used to help to identify the location of associated devices as well as users of the device. The device itself may be named or have associated metadata that, for network purposes, suggests its likely location, and may or may not correspond to the location categories in location records (e.g., "Tower wing" or "central nursing station").

In some embodiments, users have the ability to opt out and dismiss the prompt for location information. However, as noted above, those who frequently and accurately identify node locations acquire higher scores and may be targeted to provide more location inputs, while those who frequently dismiss the notifications or incorrectly identify locations may be prompted less frequently. Thus, the user score can determine the frequency of solicitation, with a minimum time between solicitations observed to avoid annoying users. Users may be incentivized to frequently and accurately identify asset location by issuing prizes (e.g., coffee cards) to users with high scores, which may be periodically reset.

Crowdsourcing may also occur indirectly, e.g., by monitoring of patients and/or access to patient-related information. For example, a node may be programmed to record patients whose information is being accessed at the node. By aggregating this information, a list of patients who are most likely to be in the vicinity of the node can be compiled. By interfacing with an ADT (admit/discharge/transfer) messages generated by the medical-records system, the room locations and patients can be cross-matched to provide the physical location of the particular patient. The location of the patient is strongly correlated to the physical location of the node as well.

Any suitable programming language may be used to implement without undue experimentation the functions described above, including those of location agent 135, with processing responsibility allocated between node 100 and server 200 as desired by the system designer. Illustratively, the programming language used may include assembly language, Ada, APL, Basic, C, C++, C*, COBOL, dBase, Forth, FORTRAN, Java, Modula-2, Pascal, Prolog, Python, RUM and/or JavaScript, for example. Further, it is not necessary that a single type of instruction or programming language be utilized in conjunction with the operation of the system and method of the invention. Rather, any number of different programming languages may be utilized as is necessary or desirable.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of establishing a location of a device in an institutional space, the method comprising the steps of:
   providing a device-location database storing records for each of a plurality of devices registered in the database as located in the institutional space, the database electronically storing, for each device, a record specifying a location of the device within the institutional space and when the location was most recently updated;
   at the device, registering a request of a user for log-on and authentication;
   in response to the request, prompting the user for authentication information and, depending on how recently the database record corresponding to the device was updated, a current location of the device;
   in response to a current location was obtained from the user, causing the current location and a time it was obtained to be stored in the database record corresponding the device
   wherein, in response to an interval between a current time and a time when the database record corresponding to the device was last updated exceeding a threshold, a plurality of users are prompted for a current location of the device, and further comprising the step of correlating the current locations provided by the plurality of users to determine consistency thereamong prior to causing the current location to be stored in the database.

2. The method of claim 1, wherein prompting the user for the current location of the device comprises providing a selection menu of location types, the location types including at least a location area and/or proximity to a fixture.

3. The method of claim 2, wherein, for the location area, the selection menu comprises identifiers of at least one of a building, a wing, a room, a floor, or a department.

4. The method of claim 2, wherein, for the fixture, the selection menu comprises identifiers of at least one of a telecommunication device, a piece of medical equipment, and a personnel station.

5. The method of claim 1, further comprising computationally maintaining, for each of a plurality of users, a score corresponding to a frequency at which the user responds to prompts for a current location, the user prompted for a current location being selected from among the plurality of users based on the user's score.

6. The method of claim 5, wherein a score also reflects precision levels of the associated user's responses.

7. The method of claim 1, wherein the threshold depends on a frequency of change to the location of the device.

8. The method of claim 1, further comprising the steps of:
obtaining from the location database a location of at least one other device associated with the device; and
determining whether the other device is proximate to the device.

9. The method of claim 8, wherein the other device is a fixed device and the user-provided current location is caused to be stored in the database only if the device is determined to be proximate to the fixed device.

10. The method of claim 8, wherein determining whether the other device is proximate to the device comprises:
wirelessly detecting, by the device and by the other device, a user's wireless device;
determining an elapsed time between the wireless detections; and
comparing the elapsed time to a threshold.

11. A system for establishing and storing locations of devices in an institutional space, the system comprising:
a plurality of devices;
a location server in operative communication with the devices and including computer storage defining a device-location database, the database including, for each device, a record specifying a location of the device within the institutional space and when the location was most recently updated, wherein
(a) each of the devices includes an authentication module and is configured to (i) register a request of a user for log-on and authentication, (ii) in response to the request, prompt the user for authentication information, and (iii) depending on how recently the database record corresponding to the device was updated, prompt the user for a current location of the device,
(b) the location server is configured to (i) receive, from the devices, current locations provided by users of the devices and times when the current locations were obtained, (ii) store the current locations in the database records corresponding to the devices, and (iii) notify a device in response to an interval between a current time and a time when the device-location database record corresponding to the device was last updated exceeding a threshold,
(c) the device is configured, in response to the threshold being exceeded, to cause the interface to prompt a plurality of users for a current location of the device and to transmit the plurality of current locations to the location server, and
(d) the location server is further configured to correlate the plurality of current locations to determine consistency thereamong prior to storing the current location in the device-location database.

12. The system of claim 11, wherein each of the devices includes a display and an interface for operating the display, the interface being configured to prompt the user for the current location by providing on the display a selection menu of location types, the location types including at least a location area and/or proximity to a fixture.

13. The system of claim 12, wherein, for the location area, the selection menu comprises identifiers of at least one of a building, a wing, a room, a floor, or a department.

14. The system of claim 12, wherein, for the fixture, the selection menu comprises identifiers of at least one of a telecommunication device, a piece of medical equipment, and a personnel station.

15. The system of claim 11, wherein the computer storage further defines a user database including, for each of a plurality of users, a score corresponding to a frequency at which the user responds to prompts for a current location, the location server being further configured to transmit, to the devices, identifiers of users who should be prompted for a current location based on the user scores.

16. The system of claim 15, wherein a user's score also reflects precision levels of the user's responses.

17. The system of claim 11, wherein the threshold depends on a frequency of change of the location of the device.

18. The system of claim 11, wherein the records of the device-location database also include, for at least some of the devices, an identifier of at least one other device associated therewith.

19. The system of claim 18, wherein, if a device associated with a current device is a fixed device, a current location received from the current device is stored in the device-location database only if the device is determined to be proximate to the fixed device.

20. The system of claim 19, wherein the location server is configured to:
receive notifications, from the device and the fixed device, of wireless detection of a user's wireless device;
determine an elapsed time between the wireless detections; and
determine whether the other device is proximate to the device by comparing the elapsed time to a threshold.

* * * * *